(12) United States Patent
Naito

(10) Patent No.: US 8,882,659 B2
(45) Date of Patent: Nov. 11, 2014

(54) ENDOSCOPIC DEVICE

(71) Applicant: Olympus Medical Systems Corp., Tokyo (JP)

(72) Inventor: Kimihiko Naito, Kawasaki (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/789,173

(22) Filed: Mar. 7, 2013

(65) Prior Publication Data

US 2013/0231531 A1    Sep. 5, 2013

Related U.S. Application Data

(63) Continuation of application No. PCT/JP2012/068345, filed on Jul. 19, 2012.

(30) Foreign Application Priority Data

Sep. 14, 2011    (JP) ................................. 2011-200982

(51) Int. Cl.
*A61B 1/04*    (2006.01)
*A61B 1/00*    (2006.01)

(52) U.S. Cl.
CPC ......... *A61B 1/00064* (2013.01); *A61B 1/00066* (2013.01); *A61B 1/00137* (2013.01); *A61B 1/00089* (2013.01)
USPC ............................ 600/129; 600/127; 600/153

(58) Field of Classification Search
CPC . A61B 1/00071; A61B 1/00089; A61B 1/008
USPC .................. 600/127, 129, 153, 156
See application file for complete search history.

(56) References Cited

U.S. PATENT DOCUMENTS 4,576,147 A * 3/1986 Hashiguchi .................... 600/129
4,879,991 A * 11/1989 Ogiu .............................. 600/129

(Continued)

FOREIGN PATENT DOCUMENTS

EP    2 116 188 A1    11/2009
JP    U-56-95201    12/1979

(Continued)

OTHER PUBLICATIONS

Aug. 30, 2013 English Translation of Written Opinion of the International Searching Authority issued in International Application No. PCT/JP2012/068345.

(Continued)

*Primary Examiner* — Anhtuan T Nguyen
*Assistant Examiner* — Jae Woo
(74) *Attorney, Agent, or Firm* — Oliff PLC

(57) ABSTRACT

An endoscopic device includes a proximal side contact portion coming into air-tight contact with an outer peripheral portion of the insertion section, and a cavity is defined between the insertion section and a fixed member to a distal direction side of the proximal side contact portion. In a protruding state of a hood, a first path which makes an inside of the hood communicate with the cavity is defined, and the hood is in air-tight contact with the fixed member over an entire circumference in circumferential directions at a distal side contact portion. In a housed state of the hood, a second path which makes the cavity to communicate with an outside of the fixed member is defined.

14 Claims, 9 Drawing Sheets

(56) References Cited

U.S. PATENT DOCUMENTS

| | | | | |
|---|---|---|---|---|
| 4,960,106 A * | 10/1990 | Kubokawa et al. | | 600/104 |
| 5,002,042 A * | 3/1991 | Okada | | 600/127 |
| 5,337,730 A * | 8/1994 | Maguire | | 600/157 |
| 5,345,339 A * | 9/1994 | Knieriem et al. | | 359/872 |
| 5,509,892 A * | 4/1996 | Bonnet | | 600/156 |
| 5,536,236 A * | 7/1996 | Yabe et al. | | 600/125 |
| 5,685,823 A * | 11/1997 | Ito et al. | | 600/127 |
| 5,695,447 A * | 12/1997 | Yabe et al. | | 600/121 |
| 5,707,344 A * | 1/1998 | Nakazawa et al. | | 600/127 |
| 5,730,701 A * | 3/1998 | Furukawa et al. | | 600/127 |
| 6,086,583 A * | 7/2000 | Ouchi | | 606/41 |
| 7,435,218 B2 * | 10/2008 | Krattiger et al. | | 600/175 |
| 7,749,160 B2 * | 7/2010 | Hirata | | 600/179 |
| 7,794,409 B2 * | 9/2010 | Damarati | | 600/565 |
| 2004/0077926 A1 * | 4/2004 | Moriyama | | 600/101 |
| 2007/0191676 A1 * | 8/2007 | Brommersma | | 600/105 |
| 2007/0191684 A1 * | 8/2007 | Hirata | | 600/179 |
| 2008/0033237 A1 * | 2/2008 | Ouchi | | 600/104 |
| 2011/0319716 A1 * | 12/2011 | Naito et al. | | 600/157 |
| 2012/0046524 A1 * | 2/2012 | Miyamoto | | 600/157 |
| 2013/0172670 A1 * | 7/2013 | Levy et al. | | 600/103 |
| 2013/0172676 A1 * | 7/2013 | Levy et al. | | 600/109 |

FOREIGN PATENT DOCUMENTS

| | | |
|---|---|---|
| JP | U-2-10517 | 1/1990 |
| JP | A-2000-79086 | 3/2000 |
| JP | A-2003-93329 | 4/2003 |
| JP | B2-3473935 | 12/2003 |
| JP | 2009-273590 | 11/2009 |
| JP | A-2010-12172 | 1/2010 |
| JP | A-2011-67650 | 4/2011 |
| WO | WO 2008/051951 A1 | 5/2008 |

OTHER PUBLICATIONS

European Search Report issued in European Patent Application No. 12832041.3 dated Dec. 12, 2013.

Sep. 11, 2012 International Search Report issued in International Application No. PCT/JP2012/068345 (with translation).

* cited by examiner

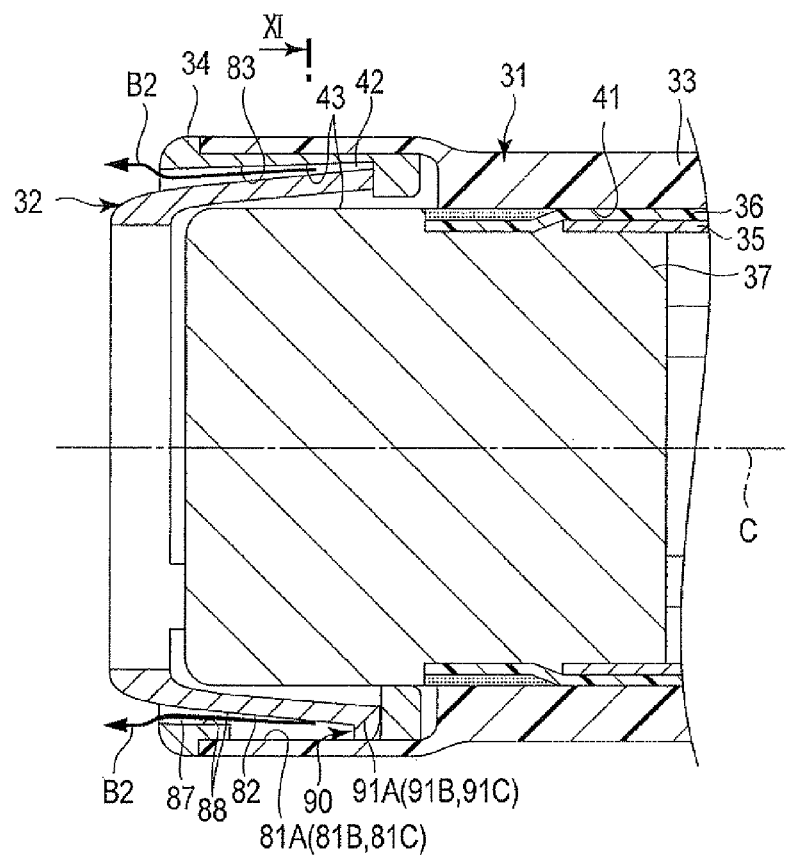
F I G. 9
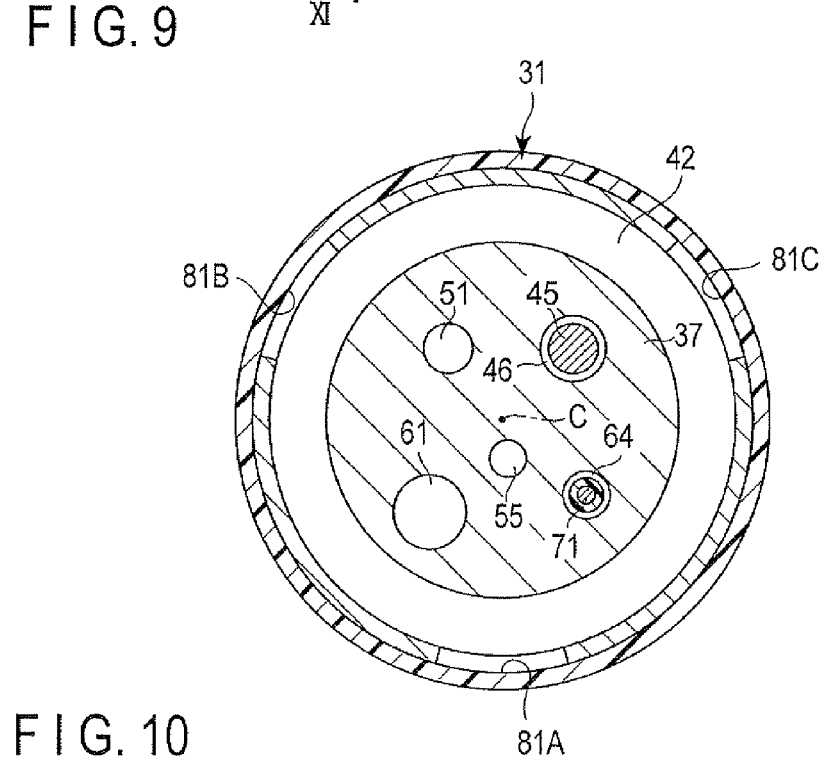
F I G. 10

ENDOSCOPIC DEVICE

CROSS-REFERENCE TO RELATED APPLICATIONS

This is a Continuation Application of PCT Application No. PCT/JP2012/068345, filed Jul. 19, 2012 and based upon and claiming the benefit of priority from prior Japanese Patent Application No. 2011-200982, filed Sep. 14, 2011, the entire contents of which are incorporated herein by reference.

BACKGROUND OF THE INVENTION

1. Field of the Invention

The present invention relates to an endoscopic device including an endoscope, and a hood attached to a distal end portion of an insertion section of the endoscope.

2. Description of the Related Art

Jpn. Pat. Appln. KOKAI Publication No. 2003-93329 discloses an endoscopic device including an endoscope, and a hood which is attached to a distal end portion of an insertion section of the endoscope. In this endoscopic device, the hood is movable along the longitudinal axis with respect to the insertion section of the endoscope. In (inside) the insertion section, a wire which is a linear member is extended along the longitudinal axis. One end of the wire is connected to the hood. When the wire moves along the longitudinal axis, the hood moves with respect to the insertion section. The hood moves between a housed (held) state where the hood is housed (held) on an outer peripheral portion of the insertion section and a protruding state where the hood is protruding toward a distal direction side from the insertion section.

Japanese Patent No. 3473935 discloses an endoscopic device including a fixed member which is fixed to a distal end portion of an insertion section of an endoscope, and a hood attached to the fixed member. In this endoscopic device, air-tightness (liquid-tightness) is maintained between an outer peripheral portion of the insertion section and the fixed member. The fixed member includes an inner cylindrical portion and an outer cylindrical portion, and an annular space is formed between the inner cylindrical portion and the outer cylindrical portion. Further, the fixed member includes a joint portion which is extended in radial directions between a proximal end of the inner cylindrical portion and a proximal end of the outer cylindrical portion. A proximal end of the annular space is closed with respect to an outside by the joint portion. A tube member which is extended on the outer peripheral portion of the insertion section along the longitudinal axis is connected to the fixed member. An inside of the tube member communicates with the annular space. When air supply to the annular space or exhaust from the annular space is carried out through the inside of the tube member, the hood moves with respect to the fixed member along the longitudinal axis. The hood moves between a housed (held) state where the hood is housed (held) in the annular space and a protruding state where the hood protrudes from the fixed member toward a distal direction side. In the protruding state of the hood, a seal ring is provided to the distal direction side of the annular space. The seal ring maintains air-tightness between the inner cylindrical portion and the outer cylindrical portion of the fixed member. Therefore, in the protruding state of the hood, air is prevented from flowing to the annular space from an inside of the hood.

BRIEF SUMMARY OF THE INVENTION

According to one aspect of the invention, an endoscopic device includes that an endoscope which includes an insertion section including a distal end portion, a proximal end portion, and an outer peripheral portion and having a longitudinal axis extended from the distal end portion to the proximal end portion; a cylindrical fixed member which includes a distal end portion, a proximal end portion, an outer peripheral portion, and an inner peripheral portion, and which is fixed to the insertion section in a state that the proximal end portion thereof contacts with the distal end portion of the insertion section; a proximal side contact portion which is provided on the inner peripheral portion of the proximal end portion of the fixed member, and which comes into air-tight contact with the outer peripheral portion of the distal end portion of the insertion section; a cavity defining portion which is formed by the outer peripheral portion of the insertion section and the inner peripheral portion of the distal end portion of the fixed member, and which defines a cavity between the outer peripheral portion of the insertion section and the inner peripheral portion of the distal end portion of the fixed member to a distal direction side of the proximal side contact portion; a cylindrical hood which is movable along the longitudinal axis with respect to the fixed member between a housed state where the hood is housed in the cavity and a protruding state where the hood is protruding toward the distal direction side from the distal end portion of the fixed member; a distal side contact portion which is provided on the inner peripheral portion of the fixed member, and with which the outer peripheral portion of the hood is in air-tight and liquid-tight contact over an entire circumference in circumferential directions in the protruding state of the hood; a first path defining portion which is formed by the inner peripheral portion of the hood and the outer peripheral portion of the insertion section, and which defines a first path configured to make an inside of the hood communicate with the cavity in the protruding state of the hood; and a second path defining portion which is formed by the inner peripheral portion of the fixed member and the outer peripheral portion of the hood, and which defines a second path configured to make the cavity to communicate with an outside of the fixed member in the housed state of the hood.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 9 is a cross-sectional view schematically showing the attachment configuration of the attachment unit with respect to the insertion section of the endoscope when the hood is in the housed state according to the first embodiment;

FIG. 10 is a cross-sectional view taken along line X-X in FIG. 8;

DETAILED DESCRIPTION OF THE INVENTION

First Embodiment

A first embodiment according to the present invention will now be described with reference to FIG. 1 to FIG. 11.

Figure 1:
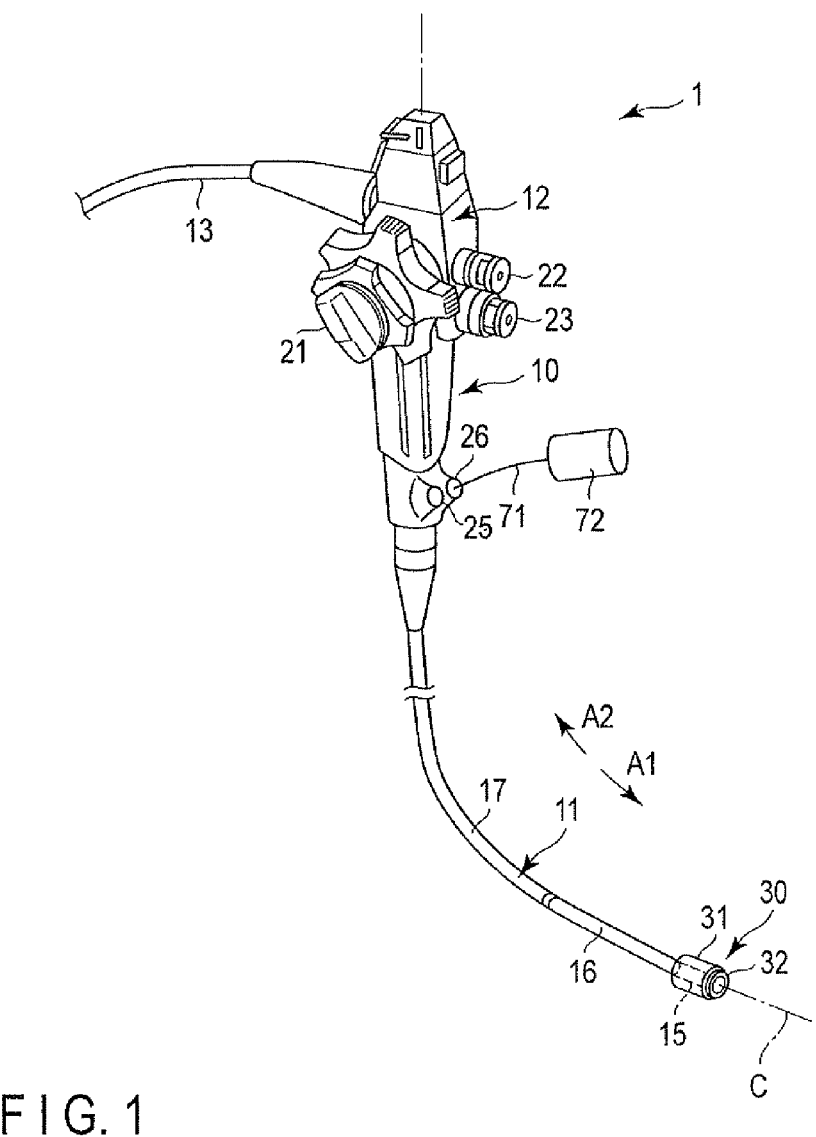
FIG. 1 is a schematic view showing an endoscopic device according to a first embodiment of the present invention.
Figure 2:
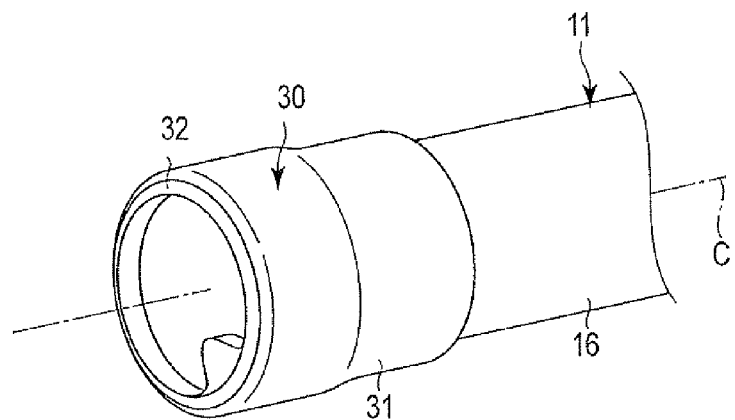
FIG. 2 is a perspective view schematically showing a distal end portion of an insertion section of an endoscope and an attachment unit when the hood is in a housed (held) state according to the first embodiment.

FIG. 1 is a view showing an endoscopic device 1 according to this embodiment. As shown in FIG. 1, the endoscopic device 1 has a longitudinal axis C. One of directions parallel to the longitudinal axis C is a distal direction (a direction of an arrow A1 in FIG. 1), and the other of the directions parallel to the longitudinal axis C is a proximal direction (a direction of an arrow A2 in FIG. 1). The endoscopic device 1 includes an endoscope 10. The endoscope 10 is extended along the longitudinal axis C, and the endoscope 10 includes an insertion section 11 which is configured to be inserted into a body cavity, and an operating section 12 provided to the proximal direction side of the insertion section 11. One end of a universal cord 13 is connected to the operating section 12. The other end of the universal cord 13 is connected to a peripheral unit such as an image processing unit, a light source unit, a liquid supply unit, or a suction unit (all of them are not shown).

The insertion section 11 includes a distal hard section 15 provided at a distal end portion of the insertion section 11, a bending section 16 which is provided to the proximal direction side of the distal hard section 15 and which is bendable, and a flexible tube section 17 which is provided to the proximal direction side of the bending section 16 and which has flexibility. Further, an attachment unit 30 is attached to the distal end portion of the insertion section 11. A bending operation knob 21 configured to perform a bending operation of bending the bending section 16 is provided to the operating section 12. In addition, a liquid supply switch 22 and a suction switch 23 are provided to the operating section 12. Furthermore, a treatment tool insertion opening 25 into which a treatment tool such as a forceps is inserted and a wire insertion opening 26 are provided to the operating section 12.

FIG. 2 to FIG. 5 are views each showing the distal end portion of the insertion section 11 and the attachment unit 30. As shown in FIG. 2 to FIG. 5, the attachment unit 30 includes a cylindrical fixed member 31 which is fixed to the distal end portion of the insertion section 11, and a cylindrical hood 32 which is movable along the longitudinal axis C with respect to the insertion section 11 and the fixed member 31. The fixed member 31 includes a soft material portion 33 made of a soft material such as an elastomer, and a high-strength portion 34 made of a material with high strength such as a resin or a metal.

Moreover, the bending section 16 includes a metallic bending tube 35, and a resin envelope tube 36 provided to an outer peripheral direction side of the bending tube 35. The envelope tube 36 forms part of the outer peripheral portion of the insertion section 11. Additionally, the distal hard portion 15 includes a columnar hard section main body 37 made of a hard material such as a metal. A distal end of the envelope tube 36 is fixed to an outer peripheral portion of the hard section main body 37 through an adhesive 39.

The soft material portion 33 of the fixed member 31 includes a proximal side contact portion 41 which is in airtight and liquid-tight contact with the outer peripheral portion (the envelope tube 36) of the insertion section 11 over an entire circumference in circumferential directions. That is, in the proximal side contact portion 41, air-tightness and liquid-tightness are maintained between the outer peripheral portion of the insertion section 11 and the fixed member 31 over the entire circumference in the circumferential directions. As a result, air (a liquid) is effectively prevented from flowing to an outside of the fixed member 31 from an inside of the fixed member 31 and an inside of the hood 32 through the proximal side contact portion 41.

A cavity 42 is provided to the distal direction side of the proximal side contact portion 41. The cavity 42 is defined by a cavity defining portion 43 between the insertion section 11 and the fixed member 31 in radial directions. That is, part of the outer peripheral portion of the insertion section 11 and part of an inner peripheral portion of the fixed member 31 form the cavity defining portion 43 which defines the cavity 42. The hood 32 is movable with respect to the fixed member 31 along the longitudinal axis C between a housed (held) state where the hood 32 is housed (held) in the cavity (a state shown in FIG. 2 and FIG. 3) and a protruding state where the hood 32 is protruding from the fixed member 31 toward the distal direction side (a state shown in FIG. 4 and FIG. 5).

Figure 3:
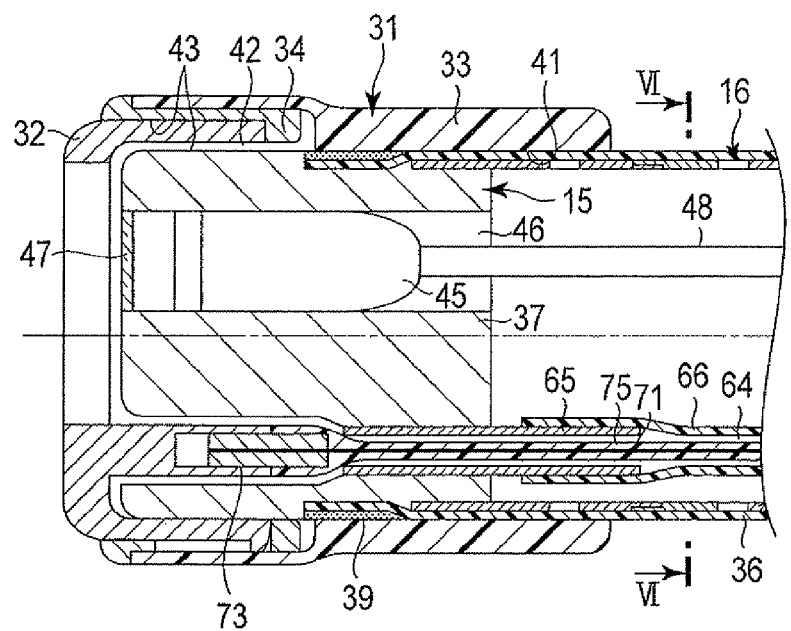
FIG. 3 is a cross-sectional view schematically showing the distal end portion of the insertion section of the endoscope and the attachment unit when the hood is in the housed state according to the first embodiment.
Figure 4:
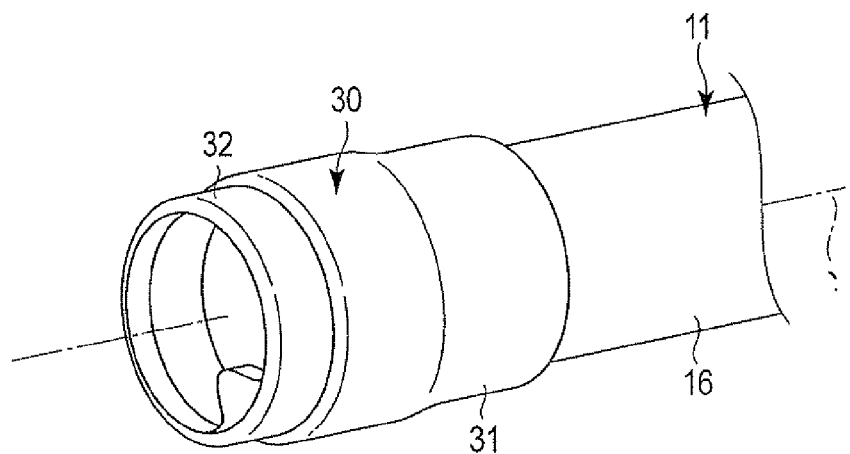
FIG. 4 is a perspective view schematically showing the distal end portion of the insertion section of the endoscope and the attachment unit when the hood is in a protruding state according to the first embodiment.
Figure 5:
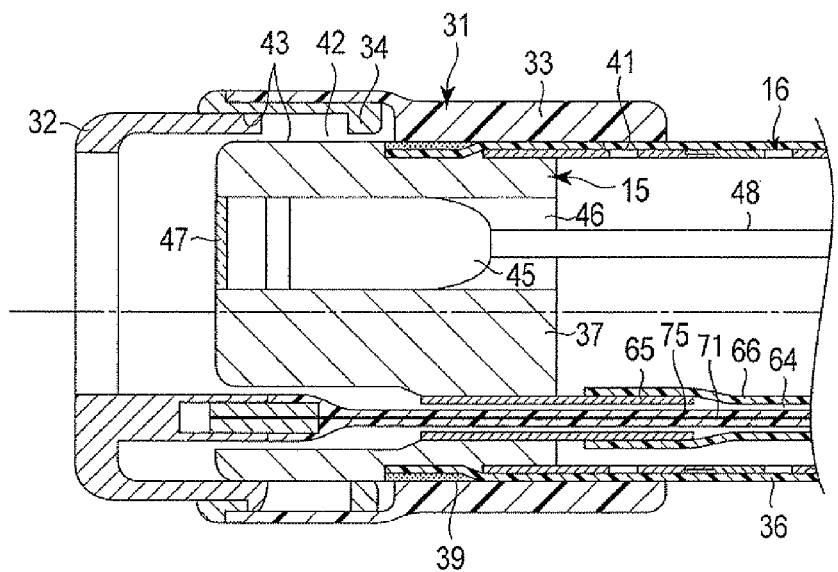
FIG. 5 is a cross-sectional view schematically showing the distal end portion of the insertion section of the endoscope and the attachment unit when the hood is in the protruding state according to the first embodiment.

As shown in FIG. 3 and FIG. 5, an imaging element 45 such as a CCD is incorporated in the hard section main body 37. The imaging element 45 is arranged in an element housing space 46 of the distal end portion of the insertion section 11. An observation window 47 is provided at a distal end of the element housing space 46. The observation window 47 is placed to the distal end portion (a distal surface of the hard section main body 37) of the insertion section 11. The imaging element 45 is configured to image a subject through the observation window 47. One end of an imaging cable 48 is connected to the imaging element 45. The imaging cable 48 is extended inside the insertion section 11 along the longitudinal axis C. Moreover, the other end of the imaging cable 48 is connected to the image processing unit (not shown), which is one of the peripheral units, through an inside of the operating section 12 and an inside of the universal cord 13.

Figure 6:
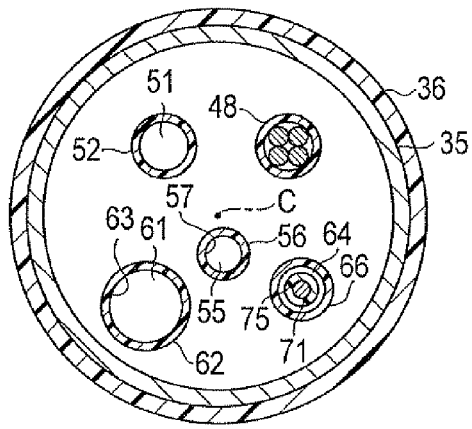
FIG. 6 is a cross-sectional view taken along line VI-VI in FIG. 3.
Figure 7:
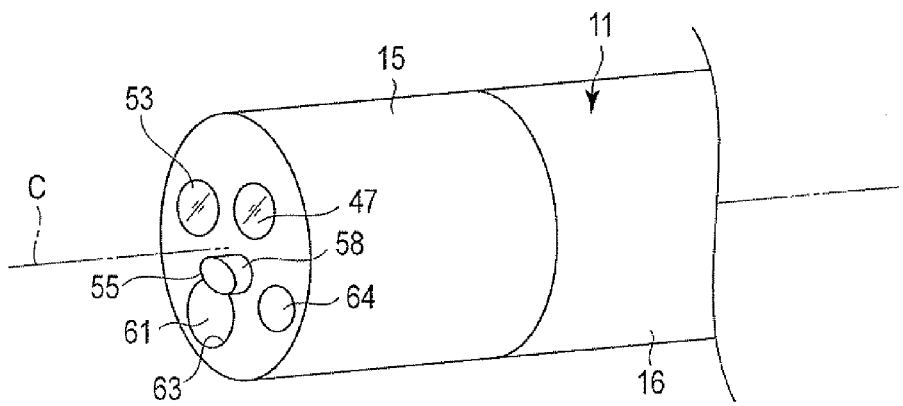
FIG. 7 is a perspective view schematically showing the distal end portion of the insertion section of the endoscope according to the first embodiment.

FIG. 6 is a cross-sectional view taken along line VI-VI in FIG. 3, and FIG. 7 is a view showing a configuration of the distal end portion of the insertion section 11. As shown in FIG. 6 and FIG. 7, a light guide portion 51 is provided in the insertion section 11. The light guide portion 51 is defined along the longitudinal axis C by part of the inner peripheral portion of the hard section main body 37 and a light guide 52. An illumination window 53 is provided at a distal end of the light guide portion 51. The illumination window 53 is placed on the distal surface of the insertion section 11 (the distal surface of the hard section main body 37). The light guide 52 is connected to the light source unit (not shown), which is one of the peripheral units, through the inside of the insertion section 11, the inside of the operating section 12, and the inside of the universal cord 13. Light exiting from the light source unit is guided by the light guide portion 51, and then is irradiated (applied) to a subject from the illumination window 53.

Additionally, a liquid supply path 55 is provided in the insertion section 11 along the longitudinal axis C. The liquid supply path 55 is defined by part of the inner peripheral portion of the hard section main body 37 and a liquid supply tube 56. That is, part of the inner peripheral portion of the hard section main body 37 and the liquid supply tube 56 form a liquid supply path defining portion 57 which defines the liquid supply path 55. A liquid supply nozzle 58 is provided at a distal end of the liquid supply path 55. The liquid supply nozzle 58 is placed on the distal surface of the insertion section 11 (the distal end portion of the insertion section 11). Further, the liquid supply tube 56 is connected to the liquid supply unit (not shown), which is one of the peripheral units, through the inside of the insertion section 11, the inside of the operating section 12, and the inside of the universal cord 13. When the hood 32 is in the protruding state, the liquid supply path 55 communicates with the inside of the hood 32. At the time of supplying a liquid such as a physiological saline solution to living tissue when the hood 32 is in the protruding state, the liquid supply unit is driven by an operation using the liquid supply switch 22. As a result, the liquid is supplied to the living tissue in the hood 32 from the liquid supply nozzle 58 through the liquid supply path 55. That is, the liquid passes through the liquid supply path 55, and then it is supplied to the inside of the hood 32 from the liquid supply nozzle 58 located to the distal end portion of the insertion section 11.

Further, a suction path 61 is provided in the insertion section 11 along the longitudinal axis C. The suction path 61 is defined by part of the inner peripheral portion of the hard section main body 37 and a suction tube 62. That is, part of the inner peripheral portion of the hard section main body 37 and the suction tube 62 serve as a suction path defining portion 63 which defines the suction path 61. The distal end of the suction path 61 is placed on the distal surface of the insertion section 11 (the distal end portion of the insertion section 11). Furthermore, the suction path 61 is extended to the inside of the operating section 12 through the inside of the insertion section 11. Moreover, the suction path 61 is bifurcated into two paths at a bifurcating portion (not shown) in the operating section 12. One of the bifurcated paths is connected to the suction unit (not shown), which is one of the peripheral units, through the inside of the universal cord 13. The other of the bifurcated paths is connected to the treatment tool insertion opening 25. Therefore, in part to the distal direction side of the bifurcating portion, the suction path 61 is also used as a treatment tool channel into which a treatment tool such as a forceps is inserted. When the hood 32 is in the protruding state, the suction path 61 communicates with the inside of the hood 32. At the time of suctioning living tissue such as a mucous membrane into the hood 32 when the hood 32 is the protruding state, the suction unit is driven by an operation using the suction switch 23. As a result, the living tissue is suctioned into the hood 32. Furthermore, a treatment (surgery) is given to the living tissue in the hood 32 by using the treatment tool inserted in the suction path 61 from the treatment tool insertion opening 25.

As shown in FIG. 3 and FIG. 5 to FIG. 7, a wire channel 64 is provided in the insertion section 11 along the longitudinal axis C. The wire channel 64 is defined by part of the inner peripheral portion of the hard section main body 37, a channel pipe 65, and a channel tube 66. The channel tube 66 is coupled with the hard section main body 37 via the channel pipe 65. The wire channel 64 is connected to the wire insertion opening 26 through the inside of the insertion section 11 and the inside of the operating section 12.

A wire 71 which is a linear member is inserted into the wire channel 64 from the wire insertion opening 26. Therefore, the wire 71 is provided in the insertion section 11 along the longitudinal axis C. One end of the wire 71 is connected to a drive portion 72 at an outside of the operating section 12. The drive portion 72 is driven by a movement operation of moving the hood 32. The drive portion 72 may be manually driven or automatically driven by transmitting an electrical signal for the movement operation. The other end of the wire 71 is connected to the hood 32 through a connecting portion 73. When the drive portion 72 is driven by the movement operation, the wire 71 moves along the longitudinal axis C. When the wire 71 moves, the hood 32 moves with respect to the fixed member 31 along the longitudinal axis C. It should be noted that an outer peripheral portion of the wire 71 is coated with a protective layer 75, and surface strength of the wire 71 is assured.

Figure 8:
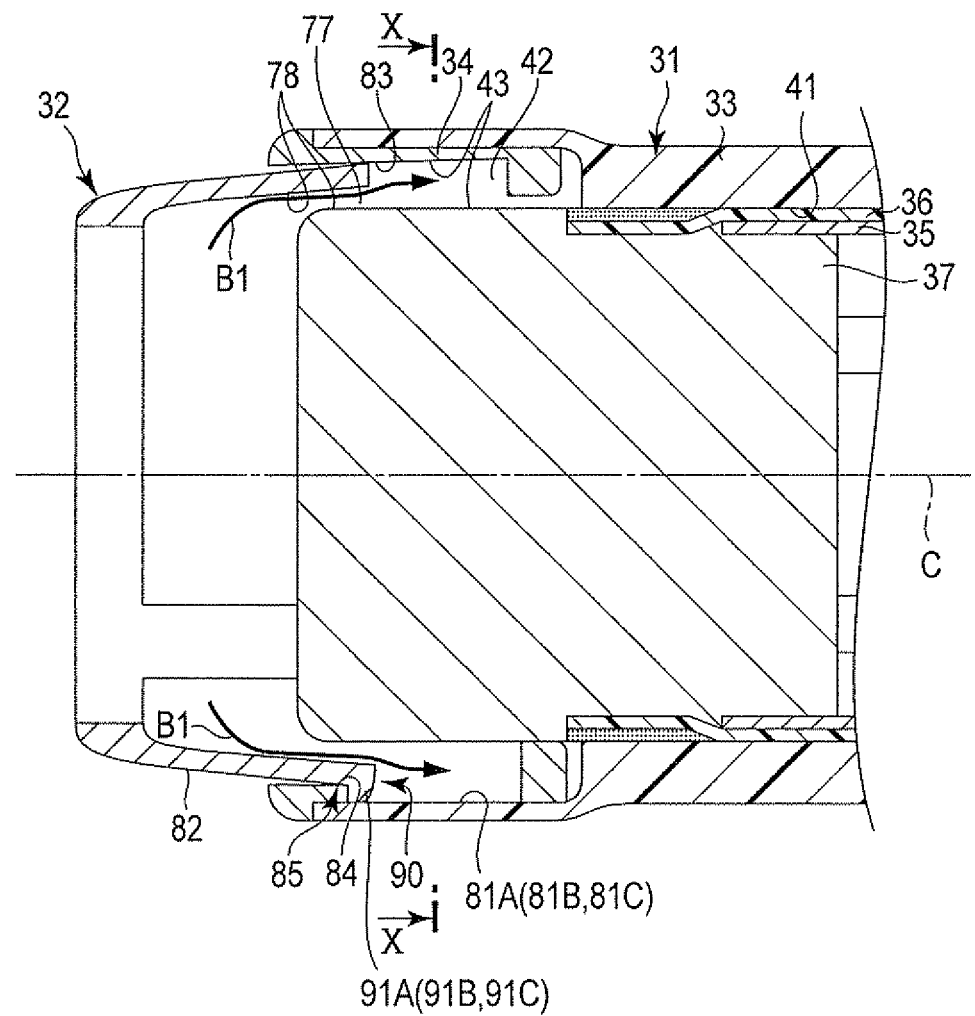
FIG. 8 is a cross-sectional view schematically showing an attachment configuration of the attachment unit with respect to the insertion section of the endoscope when the hood is in the protruding state according to the first embodiment.

FIG. 8 and FIG. 9 are a views each showing an attachment configuration of the attachment unit 30 with respect to the insertion section 11. The hood 32 is in the protruding state in FIG. 8, and the hood 32 is in the housed (held) state in FIG. 9. As shown in FIG. 8, when the hood 32 is in the protruding state, a first path 77 which makes the inside of the hood 32 communicate with the cavity 42 is formed. The first path 77 is defined between the outer peripheral portion of the hard section main body 37 and the inner peripheral portion of the hood 32. That is, part of the outer peripheral portion of the hard section main body 37 and part of the inner peripheral portion of the hood 32 form the first path defining portion 78 which defines the first path 77. The liquid, which has been supplied into the hood 32 through the liquid supply path 55 when the hood 32 is in the protruding state, passes through the first path 77 and enters the cavity 42 (an arrow B1 in FIG. 8).

Figure 11:
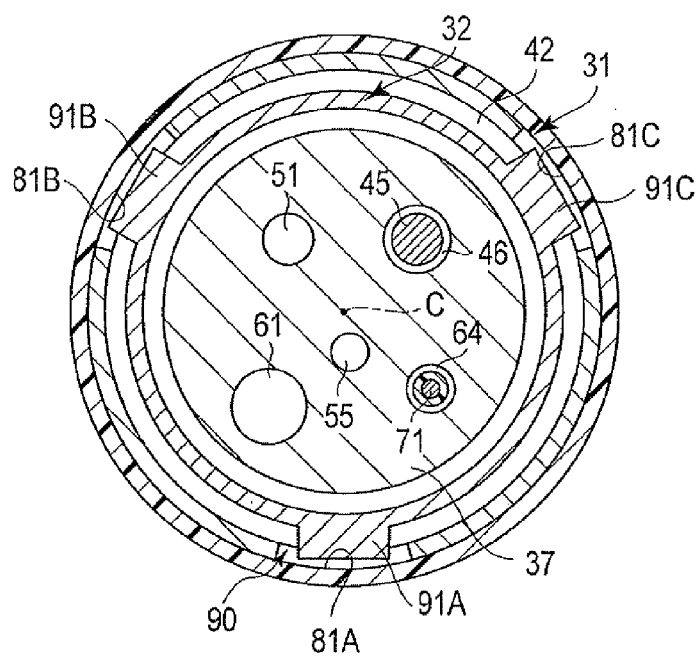
FIG. 11 is a cross-sectional view taken along line XI-XI in FIG. 9.

FIG. 10 is a cross-sectional view taken along line X-X in FIG. 8, and FIG. 11 is a cross-sectional view taken along line XI-XI in FIG. 9. As shown in FIG. 10 and FIG. 11, concave portions 81A to 81C (three in this embodiment) formed by concaving the inner peripheral portion toward the outer peripheral direction side are provided to the fixed member 31. Each of the concave portions 81A to 81C is provided over a partial range in the circumferential directions. The concave portions 81A to 81C are provided apart from each other in the circumferential directions. When the hood 32 is in the protruding state, the liquid, which has flowed into the cavity 42, stays in the concave portions 81A to 81C. That is, the concave portions 81A to 81C are liquid storage portions configured to store the liquid which has flowed into the cavity 42 when the hood 32 is in the protruding state.

As shown in FIG. 8 and FIG. 9, a taper portion 82, whose dimension from the longitudinal axis C to the outer peripheral portion is reduced as it goes toward the distal direction side, is provided to the hood 32. Further, an inner peripheral taper portion 83 is provided to the fixed member 31 over the entire range where the concave portions 81A and 81C are not provided in the circumferential directions. In the inner peripheral taper portion 83, a dimension from the longitudinal axis C to the inner peripheral portion of the fixed member 31 is reduced as it goes toward the distal direction side. When the hood 32 is in the housed state, a gap is formed between the taper portion 82 of the hood 32 and the concave portions 81A to 81C as well as the inner peripheral taper portion 83 of the fixed member 31 in the radial directions.

On the other hand, when the hood 32 is in the protruding state, an inner peripheral contact portion 84 with which the taper portion 82 is in contact over the entire circumference in the circumferential directions is provided at the distal end of the inner peripheral taper portion 83 to the distal direction side of the concave portions 81A to 81C. In the inner peripheral contact portion 84, the taper portion 82 of the hood 32 is in air-tight and liquid-tight contact with the inner peripheral portion of the fixed member 31. When the inner peripheral contact portion 84 is provided, a distal side contact portion 85 at which the fixed member 31 and the hood 32 are in air-tight and liquid-tight contact with each other over the entire circumference in the circumferential directions is formed to the distal direction side of the cavity 42.

When the distal side contact portion 85 is provided, the liquid, which has flowed into the cavity 42, is prevented from flowing out through the distal side contact portion 85 in the protruding state of the hood 32. Likewise, air is prevented from flowing to the outside of the fixed member 31 from the cavity 42 through the distal side contact portion 85. Furthermore, as described above, at the proximal side contact portion 41, the air-tightness and the liquid-tightness are maintained between the outer peripheral portion of the insertion section 11 and the fixed member 31 over the entire circumference in the circumferential directions. Therefore, the liquid, which has flowed into the cavity 42, is prevented from flowing out through the proximal side contact portion 41. Likewise, the air is prevented from flowing to the outside of the fixed member 31 from the cavity 42 through the proximal side contact portion 41.

As shown in FIG. 9, when the hood 32 is in the housed state, the distal side contact portion 85 is not formed. Therefore, a second path 87 configured to make the cavity 42 and the outside of the fixed member 31 to communicate with each other is formed to the distal direction side of the cavity 42. The second path 87 is defined between the outer peripheral portion of the hood 32 and the inner peripheral portion of the fixed member 31. That is, part of the outer peripheral portion of the hood 32 and, part of the inner peripheral portion of the fixed member 31 form a second path defining portion 88 which defines the second path 87. When the hood 32 moves from the protruding state to the housed state, the liquid stored in the concave portions (the liquid storage portions) 81A to 81C flows to the outside of the fixed member 31 through the second path 87 (an arrow B2 in FIG. 9).

Moreover, as shown in FIG. 11, convex portions 91A to 91C (three in this embodiment) formed by convexing the outer peripheral portion toward the outer peripheral direction are provided to the hood 32. The number of the convex portions 91A to 91C is equal to the number of the concave portions 81A to 81C, and the convex portions 91A to 91C are apart from each other in the circumferential directions. In accordance with the movement of the hood 32, each of the convex portions 91A to 91C moves in the corresponding concave portion 81A to 81C along the longitudinal axis C. When each of the convex portions 91A to 91C abuts on the distal end of the corresponding concave portion 81A to 81C, the movement of each of the convex portions 91A to 91C toward the distal direction is restricted. Likewise, when each of the convex portions 91A to 91C abuts on the proximal end of the corresponding concave portion 81A to 81C, the movement of each of the convex portions 91A to 91C toward the proximal direction is restricted. When the movement of each of the convex portions 91A to 91C is restricted, a movement range of the hood 32 along the longitudinal axis C is adjusted. As described above, the concave portions 81A to 81C and the convex portions 91A to 91C constitute a movement range adjustment portion 90 configured to adjust the movement range of the hood 32 along the longitudinal axis C.

A function of the endoscopic device 1 according to this embodiment will now be described. At the time of moving the hood 32 to the protruding state, when the drive portion 72 is driven by a movement operation, the wire 71 is moved toward the distal direction. In accordance with the movement of the wire 71, the hood 32 moves with respect to the fixed member 31 in the distal direction. Further, when the hood 32 moves to the protruding state, each of the convex portions 91A to 91C of the hood 32 abuts on the distal end of the corresponding concave portion 81A to 81C of the fixed member 31. As a result, the movement range of the hood 32 is adjusted.

In the protruding state of the hood 32, living tissue such as a mucous membrane is suctioned into the hood 32, and a treatment is given to the suctioned living tissue in the hood 32. In the protruding state of the hood 32, the suction path 61 communicates with the inside of the hood 32. Therefore, when the suction unit is driven by an operation using the suction switch 23, air is suctioned (drawn) through the suction path 61. As a result, the living tissue is suctioned into the hood 32. Furthermore, while a treatment tool inserted into the suction path 61 from the treatment tool insertion opening 25 is used, a treatment (surgery) of the suctioned living tissue is carried out in the hood 32.

Here, at the proximal side contact portion 41 provided to the proximal direction side of the cavity 42, the air-tightness is maintained between the outer peripheral portion of the insertion section 11 and the fixed member 31 over the entire circumference in the circumferential directions. Therefore, air is prevented from flowing to the outside of the fixed member 32 from the cavity 42 through the proximal side contact portion 41. Further, in the protruding state of the hood 32, the distal side contact portion 85, at which the fixed member 31 and the hood 32 are in air-tight and liquid-tight contact with each other over the entire circumference in the circumferential directions, is formed to the distal direction side of the cavity 42. Therefore, in the protruding state of the hood 32, the air is prevented from flowing to the outside of the fixed member 31 from the cavity 42 through the distal side contact portion 85. As described above, in the protruding state of the hood 32, the proximal side contact portion 41 and the distal side contact portion 85 effectively prevent the air from flowing to the outside of the fixed member 31 from the inside of the hood 32 and the cavity 42. Therefore, in the protruding state of the hood 32, performance of suctioning living tissue into the hood 32 can be assured.

Moreover, in the protruding state of the hood 32, a liquid is supplied to the living tissue suctioned in the hood 32. When the liquid supply unit is driven by an operation using the liquid supply switch 22, the liquid is supplied to the living tissue in the hood 32 from the liquid supply nozzle 58 through the liquid supply path 55. Here, in the protruding state of the hood 32, the first path 77 configured to make the inside of the hood 32 communicate with the cavity 42 is formed. In the protruding state of the hood 32, the liquid, which has been supplied into the hood 32 through the liquid supply path 55, flows into the cavity 42 via the first path 77 (arrow B1 in FIG. 8).

Additionally, the concave portions 81A to 81C formed by concaving the inner peripheral portion toward the outer peripheral direction side are provided to the fixed member 31. In the protruding state of the hood 32, the liquid, which has flowed into the cavity 42, is stored in the concave portions 81A to 81C. As described above, when the hood 32 is in the protruding state, the liquid supplied into the hood 32 flows into the cavity 42 through the first path 77, and it is apt to be stored in the concave portions 81A to 81C. It should be noted that, when the hood 32 is in the protruding state, the proximal side contact portion 41 and the distal side contact portion 85 prevent the liquid stored in the concave portions 81A to 81C from flowing to the outside of the fixed member 31.

Further, at the time of moving the hood 32 to the housed (held) state, when the drive portion 72 is driven by the movement operation, the wire 71 is moved toward the proximal direction. In accordance with the movement of the wire 71, the hood 32 moves in the proximal direction with respect to the fixed member 31. Furthermore, when the hood 32 moves to the housed state, each of the convex portions 91A to 91C of the hood 32 abuts on the proximal end of the corresponding concave portion 81A to 81C of the fixed member 31. As a result, the movement range of the hood 32 is adjusted.

When the hood 32 is in the housed state, the distal side contact portion 85 is not formed. Therefore, the second path 87 configured to make the cavity 42 communicate with the outside of the fixed member 31 is formed to the distal direction side of the cavity 42. When the hood 32 moves from the protruding state to the housed state, the liquid stored in the concave portions (the liquid storage portions) 81A to 81C flows to the outside of the fixed member 31 through the second path 87 (arrow 32 in FIG. 9).

In the endoscopic device 1 described above, when the hood 32 is in the protruding state, the supplied liquid is allowed to flow from the inside of the hood 32 to the cavity 42 through the first path 77, and the flowed liquid is stored in the concave portions 81A to 81C of the cavity 42. Furthermore, when the hood 32 is moved to the housed state, the stored liquid is allowed to flow to the outside of the fixed member 31 from the cavity 42 through the second path 87. Therefore, in the housed state of the hood 32, the liquid hardly stays in the hood 32. Therefore, in the housed state of the hood 32, the liquid hardly adheres to the distal surface of the insertion section 11. In the housed state of the hood 32, a subject is imaged by the imaging element 45 through the observation window 47. When the configuration in which the liquid hardly adheres to the distal surface of the insertion section 11 is adopted, visibility is improved at the time of observing a subject by using the imaging element in the housed state of the hood 32.

Therefore, the thus configured endoscopic device 1 exerts the following effect. That is, in the endoscopic device 1 according to this embodiment, the air-tightness is maintained between the outer peripheral portion of the insertion section 11 and the fixed member 31 over the entire circumference in the circumferential directions at the proximal side contact portion 41 provided to the proximal direction side of the cavity 42. Therefore, the air is prevented from flowing to the outside of the fixed member 31 from the cavity 42 through the proximal side contact portion 41. Moreover, in the protruding state of the hood 32, the distal side contact portion 85, at which the fixed member 31 and the hood 32 are in air-tight and liquid-tight contact with each other over the entire circumference in the circumferential directions, is formed to the distal direction side of the cavity 42. Therefore, in the protruding state of the hood 32, the air is prevented from flowing to the outside of the fixed member 31 from the cavity 42 through the distal side contact portion 85. As described above, in the protruding state of the hood 32, the proximal side contact portion 41 and the distal side contact portion 85 effectively prevent the air from flowing to the outside of the fixed member 31 from the inside of the hood 32 and the cavity 42. Therefore, in the protruding state of the hood 32, the performance of suctioning living tissue into the hood 32 can be assured.

Additionally, in the endoscopic device 1, when the hood 32 is in the protruding state, the supplied liquid is allowed to flow to the cavity 42 from the inside of the hood 32 through the first path 77, and the in-flowed liquid is stored in the concave portions 81A to 81C of the cavity 42. Further, when the hood 32 is moved to the housed state, the stored liquid is allowed to flow to the outside of the fixed member 31 from the cavity 42 through the second path 87. Therefore, in the housed state of the hood 32, the liquid hardly remains in the hood 32. Therefore, in the housed state of the hood 32, the liquid hardly adheres to the distal surface of the insertion section 11. Since the liquid hardly adheres to the distal surface of the insertion section 11, visibility can be improved at the time of observing a subject by using the imaging element 45 in the housed state of the hood 32.

Modification of First Embodiment

Figure 12:
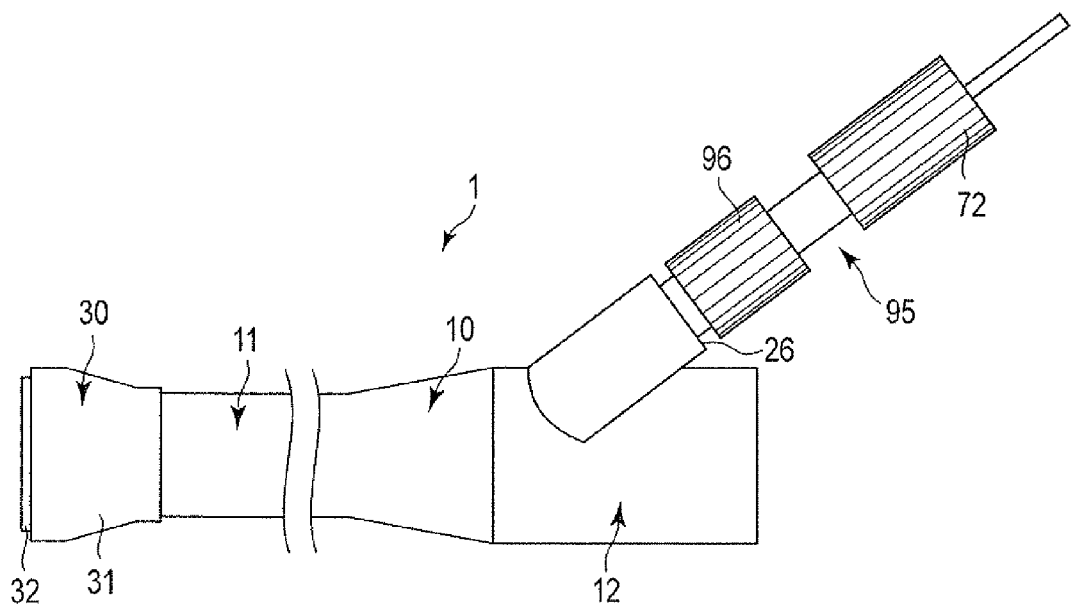
FIG. 12 is a schematic view showing an endoscopic device when a hood is in a housed state according to a first modification of the first embodiment.
Figure 13:
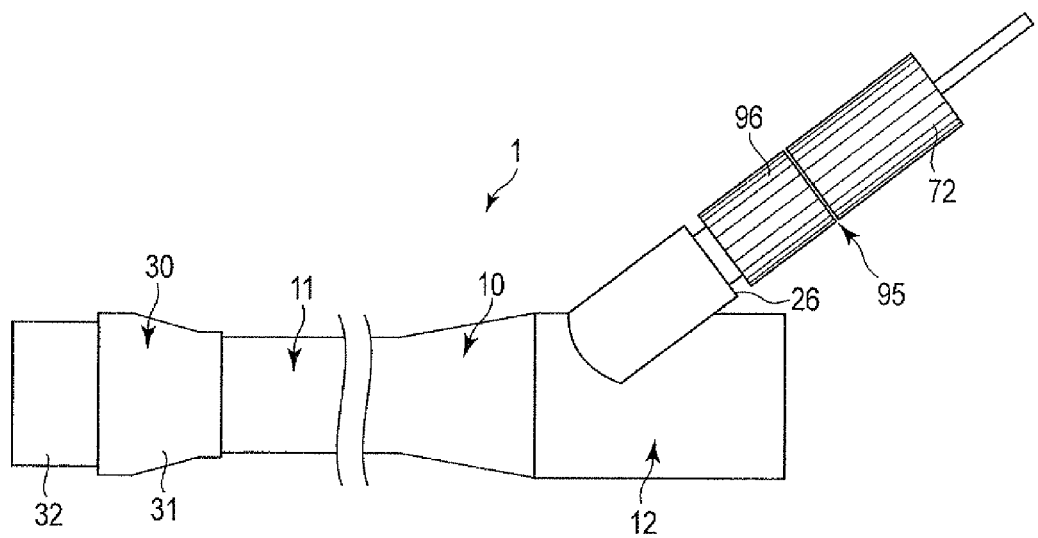
FIG. 13 is a schematic view showing the endoscopic device when the hood is in a protruding state according to the first modification of the first embodiment.

It should be noted that, in the first embodiment, the movement range of the hood 32 is adjusted by the concave portions 81A to 81C and the convex portions 91A to 91C (the movement range adjustment portion 90), but the present invention is not limited thereto. For example, as shown in FIG. 12 and FIG. 13 as a first modification of the first embodiment, a movement range adjustment portion 95 may be provided. The movement range adjustment portion 95 according to this modification includes a regulating portion 96 which is provided to the operating section 12 of the endoscope 10 or fixed to the operating section 12. Further, when the drive portion 72 is driven, the drive portion 72 moves integrally with the wire 71. When the hood 32 is moved from the housed (held) state shown in FIG. 12 to the protruding state shown in FIG. 13, the drive portion 72 abuts on the regulating portion 96. As a result, movement of the drive portion 72 in the distal direction is regulated. That is, the regulating portion 96 is configured to regulate the movement range of the drive portion 72. When the movement range of the drive portion 72 is regulated, the movement range of the hood 32 is adjusted.

In this modification, since the movement range adjustment portion 95 configured to adjust the movement range of the hood 32 is provided to the operating section 12, as different from the first embodiment, the convex portions 91A to 91C do not have to be provided to the hood 32. Therefore, the diameter of the hood 32 is reduced. When the diameter of the hood 32 is reduced, the diameter of a distal end portion of the endoscopic device 1 is decreased.

Further, in the first embodiment, the three concave portions 81A to 81C are provided, but the present invention is not limited thereto. Any configuration can suffice as long as at least one concave portion (81A to 81C) formed by concaving the inner peripheral portion of the fixed member 31 toward the outer peripheral direction side is provided over a partial range in the circumferential directions. Furthermore, the supplied liquid can be allowed to flow into the cavity 42 from the inside of the hood 32 through the first path 77 in the protruding state of the hood 32, and the in-flowed liquid can be stored in the concave portion (81A to 81C) of the cavity 42.

Second Embodiment

A second embodiment according to the present invention will now be described with reference to FIG. 14 and FIG. 15. It should be noted like reference numerals denote the same parts or parts having the same functions as those in the first embodiment, a description thereof will be omitted.

Figure 14:
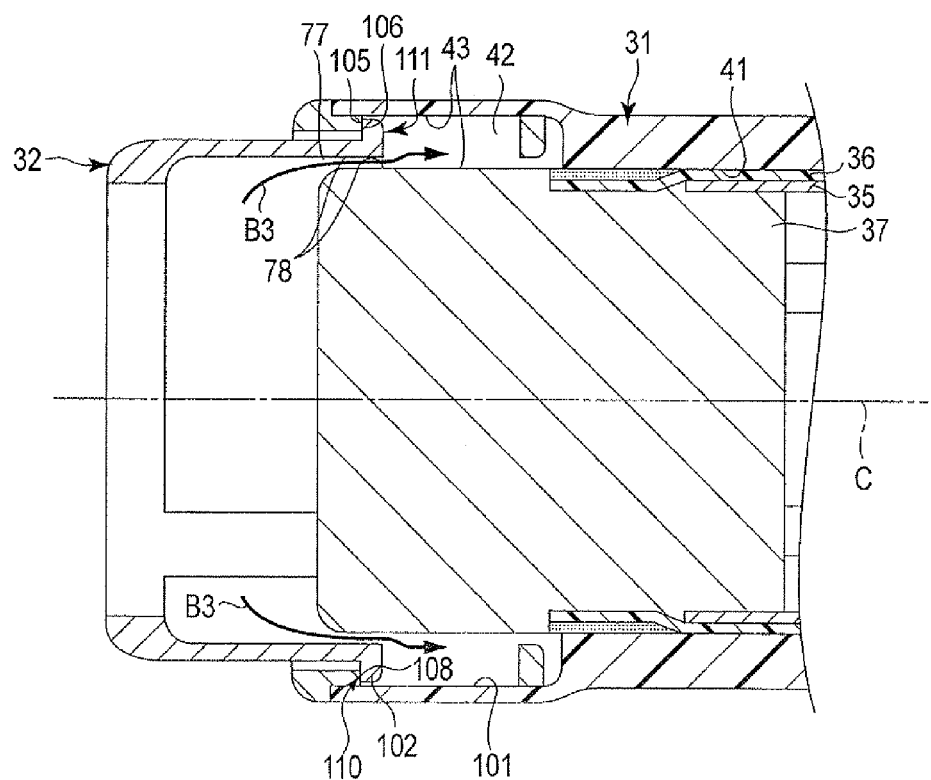
FIG. 14 is a cross-sectional view schematically showing an attachment configuration of an attachment unit with respect to an insertion section of an endoscope when a hood is in a protruding state according to a second embodiment of the present invention.
Figure 15:
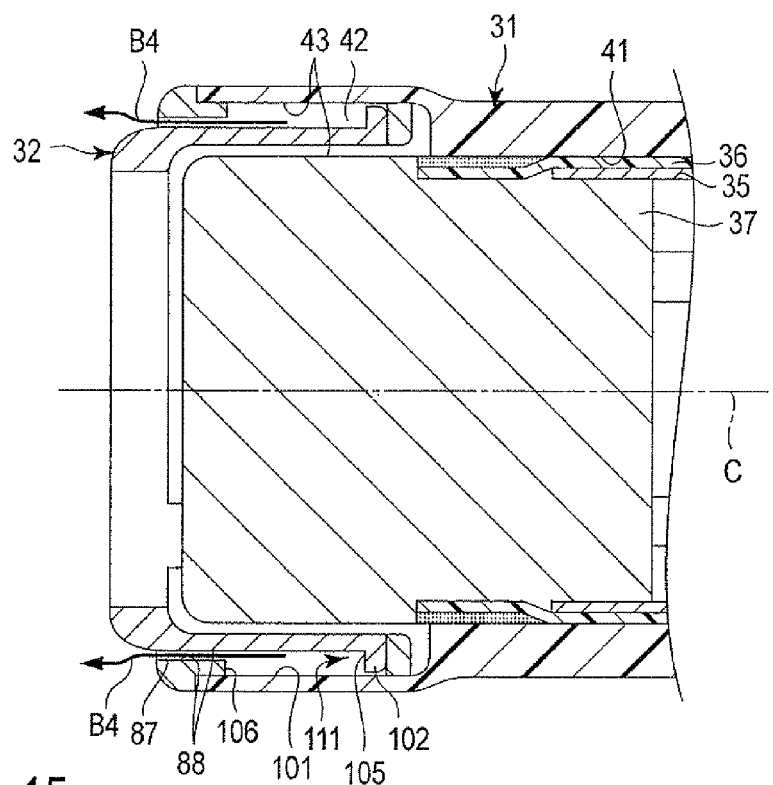
FIG. 15 is a cross-sectional view schematically showing the attachment configuration of the attachment unit with respect to the insertion section of the endoscope when the hood is in a housed state according to the second embodiment.

FIG. 14 and FIG. 15 are views each showing an attachment configuration of an attachment unit 30 with respect to an insertion section 11. A hood 32 is in a protruding state in FIG. 14, and the hood 32 is in a housed (held) state in FIG. 15. As shown in FIG. 14 and FIG. 15, in an endoscopic device 1 according to this embodiment, like the first embodiment, a cavity 42 is provided between the insertion section 11 and a fixed member 31 in radial directions. Furthermore, a proximal side contact portion 41 is provided to the proximal direction side of the cavity 42. At the proximal side contact portion 41, an outer peripheral portion of the insertion section 11 is in air-tight (liquid-tight) contact with the fixed member 31 over the entire circumferential in circumferential directions. Therefore, like the first embodiment, air is prevented from flowing to the outside of the fixed member 31 from the cavity 42 through the proximal side contact portion 41.

Moreover, as shown in FIG. 14, when the hood 32 is in the protruding state, like the first embodiment, a first path 77 configured to make the inside of the hood 32 communicate with the cavity 42 is formed. The first path 77 is defined between the outer peripheral portion of the hard section main body 37 and the inner peripheral portion of the hood 32. A liquid, which has been supplied into the hood 32 through a liquid supply path 55 when the hood 32 is in the protruding state, flows into the cavity 42 through the first path 77 (an arrow 53 in FIG. 14).

As shown in FIG. 14 and FIG. 15, a concave portion 101 formed by concaving the inner peripheral portion toward the outer peripheral direction side is provided to the fixed member 31. The concave portion 101 is provided over the entire circumference in the circumferential directions. When the hood 32 is in the protruding state, the liquid, which has flowed into the cavity 42, is stored in the concave portion 101. That is, the concave portion 101 serves as a liquid storage portion configured to store the liquid, which has flowed into the cavity 42, when the hood 32 is in the protruding state.

Additionally, a convex portion 102 formed by protruding the outer peripheral portion toward the outer peripheral direction side is provided to the hood 32. The convex portion 102 is provided over the entire circumference in the circumferential directions. In accordance with the movement of the hood 32, the convex portion 102 moves in the concave portion 101 along the longitudinal axis C. A gap is provided in the radial directions between the convex portion 102 of the hood 32 and the concave portion 101 of the fixed member 31.

An abutting surface 105 perpendicular to the longitudinal axis C is provided at a distal end of the convex portion 102. Further, a receiving surface 106 perpendicular to the longitudinal axis C is provided at a distal end of the concave portion 101. When the hood 32 is in the protruding state, the abutting surface 105 abuts on the receiving surface 106. As a result, an inner peripheral contact portion 108 with which the convex portion 102 is in contact over the entire circumference in the circumferential directions is formed at the distal end of the concave portion 101 when the hood 32 is in the protruding state. In the inner peripheral contact portion 108, the abutting surface 105 of the convex portion 102 of the hood 32 is in air-tight and liquid-tight contact with the receiving surface 106 of the concave portion 101. When the inner peripheral contact portion 108 is provided, a distal side contact portion 110, at which the fixed member 31 is in air-tight and liquid-tight contact with the hood 32 over the entire circumference in the circumferential directions, is formed to the distal direction side of the cavity 42.

When the distal side contact portion 110 is provided, in the protruding state of the hood 32, a liquid, which has flowed into the cavity 42, is prevented from flowing out through the distal side contact portion 110. Likewise, air is prevented from flowing to the outside of the fixed member 31 from the cavity 42 through the distal side contact portion 110. Further, as described above, at the proximal side contact portion 41, air-tightness and liquid-tightness are maintained between the outer peripheral portion of the insertion section 11 and the fixed member 31 over the entire circumference in the circumferential directions. Therefore, the liquid, which has flowed into the cavity 42, is prevented from flowing out through the proximal side contact portion 41. Likewise, the air is prevented from flowing to the outside of the fixed member 31 from the cavity 42 through the proximal side contact portion 41.

As shown in FIG. 15, when the hood 32 is in the housed state, the distal side contact portion 110 is not formed. Therefore, like the first embodiment, a second path 87 configured to make the cavity 42 communicate with the outside of the fixed member 31 is formed to the distal direction side of the cavity 42. The second path 87 is defined between the outer peripheral portion of the hood 32 and the inner peripheral portion of the fixed member 31. When the hood 32 is moved from the protruding state to the housed state, the liquid stored in the concave portion (a liquid storage portion) 101 flows to the outside of the fixed member 31 through the second path 87 (an arrow B4 in FIG. 15).

Furthermore, as described above, in accordance with the movement of the hood 32, the convex portion 102 moves in the concave portion 101 along the longitudinal axis C. When the convex portion 102 abuts on the distal end of the concave portion 101, the movement of the convex portion 102 toward the distal direction is restricted. Likewise, when the convex portion 102 abuts on the proximal end of the concave portion 101, the movement of the convex portion 102 toward the proximal direction is restricted. When the movement of the convex portion 102 is restricted, a movement range of the hood 32 along the longitudinal axis C is adjusted. As described above, the concave portion 101 and the convex portion 102 function as a movement range adjustment portion 111 configured to adjust the movement range of the node 32 along the longitudinal axis C.

A function of the endoscopic device 1 according to this embodiment will now be described. In case of moving the hood 32 to the protruding state, when a drive portion 72 is driven by a movement operation, a wire 71 is moved toward the distal direction. In accordance with the movement of the wire 71, the hood 32 moves toward the distal direction with respect to the fixed member 31. Moreover, when the hood 32 moves to the protruding state, the convex portion 102 of the hood 32 abuts on the distal end of the concave portion 101 of the fixed member 31. As a result, a movement range of the hood 32 is adjusted.

When the hood 32 is in the protruding state, living tissue such as a mucous membrane is suctioned into the hood 32, and a treatment is given to the suctioned living tissue in the hood 32. When the hood 32 is in the protruding state, a suction path 61 communicates with the inside of the hood 32. Therefore, when a suction unit is driven by an operation using a suction switch 23, air is suctioned (drawn) through the suction path 61. As a result, the living tissue is suctioned into the hood 32. Additionally, a treatment (surgery) is given to the suctioned living tissue in the hood 32 by using a treatment tool inserted into the suction path 61 from a treatment tool insertion opening 25.

Here, at the proximal side contact portion 41 provided to the proximal direction side of the cavity 42, air-tightness is maintained between the outer peripheral portion of the insertion section 11 and the fixed member 31 over the entire circumference in the circumferential directions. Therefore, air is prevented from flowing to the outside of the fixed member 31 from the cavity 42 through the proximal side contact portion 41. Further, when the hood 32 is in the protruding state, a distal side contact portion 110, at which the fixed member 31 and the hood 32 are in air-tight and liquid-tight contact with each other over the entire circumference in the circumferential directions, is formed to the distal direction side of the cavity 42. Therefore, when the hood 32 is in the protruding state, the air is prevented from flowing to the outside of the fixed member 31 from the cavity 42 through the distal side contact portion 110. As described above, when the hood 32 is in the protruding state, the proximal side contact portion 41 and the distal side contact portion 110 effectively prevent the air from flowing to the outside of the fixed member 31 from the inside of the hood 32 and the cavity 42. Therefore, when the hood 32 is in the protruding state, performance of suctioning living tissue into the hood 32 can be assured.

Furthermore, when the hood 32 is in the protruding state, at the distal side contact portion 110, the abutting surface 105 of the convex portion 102 abuts on the receiving surface 106 of the concave portion 101. The abutting surface 105 is perpendicular to the longitudinal axis C, and the receiving surface 106 is perpendicular to the longitudinal axis C. Here, in case of moving the hood 32 from the housed state to the protruding state, the wire 71 moves toward the distal direction. Therefore, force toward the distal direction parallel to the longitudinal axis C is applied to the hood 32 from the wire 71 through a connecting portion 73. Thus, at the distal side contact portion 110 where the abutting surface 105 perpendicular to the longitudinal axis C abuts on the receiving surface 106 perpendicular to the longitudinal axis C, the force in the distal direction, which is applied to the hood 32, achieves firm close contact between the abutting surface 105 and the receiving surface 106. Therefore, at the distal side contact portion 110, the air-tightness is further assuredly maintained. Accordingly, the air can be further effectively prevented from flowing to the outside of the fixed member 31 from the inside of the hood 32 and the cavity 42.

Further, when the hood 32 is in the protruding state, the liquid is supplied to living tissue suctioned into the hood 32. When the liquid supply unit is driven by an operation using the liquid supply switch 22, the liquid is supplied to the living tissue in the hood 32 from the liquid supply nozzle 58 through the liquid supply path 55. Here, when the hood 32 is in the protruding state, the first path 77 configured to make the inside of the hood 32 communicate with the cavity 42 is formed. In the protruding state of the hood 32, The liquid, which has been supplied into the hood 32 through the liquid supply path 55, flows into the cavity 42 through the first path 77 (arrow B3 in FIG. 14).

Furthermore, the concave portion 101 formed by concaving the inner peripheral portion toward the outer peripheral direction side is provided to the fixed member 31. When the hood 32 is in the protruding state, the liquid, which has flowed into the cavity 42, is stored in the concave portion 101. As described above, when the hood 32 is in the protruding state, the liquid, which has been supplied into the hood 32, flows into the cavity 42 through the first path 77, and it is apt to be stored in the concave portion 101. It should be noted that, when the hood 32 is in the protruding state, the proximal side contact portion 41 and the distal side contact portion 110 prevent the liquid stored in the concave portion 101 from flowing to the outside of the fixed member 31.

Moreover, in case of moving the hood 32 to the housed state, when the drive portion 72 is driven by a movement operation, the wire 71 is moved in the proximal direction. In accordance with the movement of the wire 71, the hood 32 moves toward the proximal direction with respect to the fixed member 31. Additionally, when the hood 32 moves to the housed state, the convex portion 102 of the hood 32 abuts on the proximal end of the concave portion 101 of the fixed member 31. As a result, the movement range of the hood 32 is adjusted.

When the hood 32 is in the housed state, the distal side contact portion 110 is not formed. Therefore, the second path 87, configured to make the cavity 42 communicate with the outside of the fixed member 31, is formed to the distal direction side of the cavity 42. When the hood 32 moves from the protruding state to the housed state, the liquid stored in the concave portion (the liquid storage portion) 101 flows to the outside of the fixed member 31 through the second path 87 (arrow B4 in FIG. 15).

In the above-described endoscopic device 1, when the hood 32 is in the protruding state, the supplied liquid is allowed to flow to the cavity 42 from the inside of the hood 32 through the first path 77, and the in-flowed liquid is stored in the concave portion 101 of the cavity 42. Further, when the hood 32 is moved to the housed state, the stored liquid is allowed to flow to the outside of the fixed member 31 from the cavity 42 through the second path 87. Therefore, in the housed state of the hood 32, the liquid hardly remains in the hood 32. Therefore, in the housed state of the hood 32, the liquid hardly adheres to the distal surface of the insertion section 11. In the housed state of the hood 32, a subject is imaged by an imaging element 45 through an observation window 47. When the configuration where the liquid hardly adheres to the distal surface of the insertion section is adopted, visibility is improved at the time of observing a subject using the imaging element 45 in the housed state of the hood 32.

Thus, in the thus configured endoscopic device 1, in addition to the same effect as that of the first embodiment, the following effect can be exercised. That is, in the endoscopic device 1 according to this embodiment, the abutting surface 105 perpendicular to the longitudinal axis C is provided to the convex portion 102 of the hood 32, and the receiving surface 106 perpendicular to the longitudinal axis C is provided to the concave portion 101 of the fixed member 31. Moreover, in the protruding state of the hood 32, at the distal side contact portion 110, the abutting surface 105 of the convex portion 102 abuts on the receiving surface 106 of the concave portion 101. Here, in case of moving the hood 32 from the housed state to the protruding state, the wire 71 moves toward the distal direction. Therefore, force in the distal direction that is parallel to the longitudinal axis C is applied to the hood 32 from the wire 71 through the connecting portion 73. Therefore, at the distal side contact portion 110 where the abutting surface 105 perpendicular to the longitudinal axis C abuts on the receiving surface 106 perpendicular to the longitudinal axis C, the force in the distal direction, which is applied to the hood 32, achieves stiff close contact between the abutting surface 105 and the receiving surface 106. Therefore, at the distal side contact portion 110, the air-tightness is further assuredly maintained. Accordingly, the air can be further effectively prevented from flowing to the outside of the fixed member 31 from the inside of the hood 32 and the cavity 42.

Modification of Second Embodiment

Figure 16:
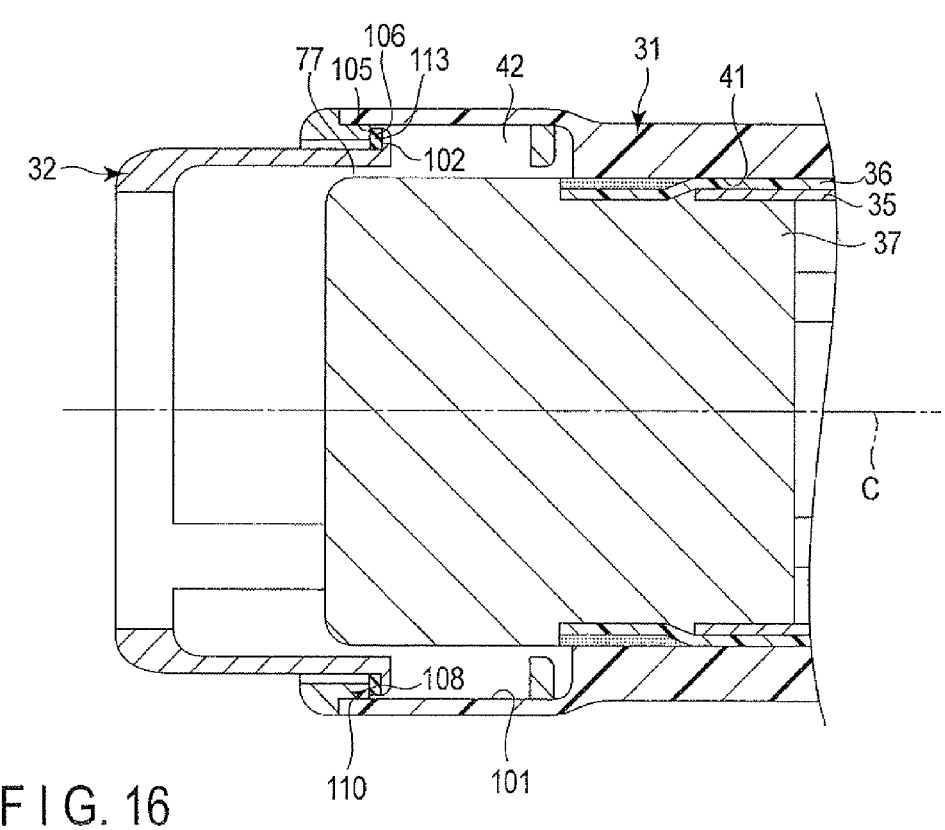
FIG. 16 is a cross-sectional view schematically showing an attachment configuration of an attachment unit with respect to an insertion section of an endoscope when a hood is in a protruding state according to a first modification of the second embodiment.

It should be noted that, as a first modification of the second embodiment, the convex portion 102 of the hood 32 may include an elastic portion 113 made of an elastic material such as a rubber as shown in FIG. 16. In this modification, the abutting surface 105 is formed by the elastic portion 113. Further, when the hood 32 is in the protruding state, the abutting surface 105 of the elastic portion 113 abuts on the receiving surface 106 of the concave portion 101 of the fixed member 31. That is, in the protruding state of the hood 32, the elastic portion 113 of the convex portion 102 is elastically in contact with the inner peripheral contact portion 108 of the fixed member 31.

Since the elastic portion 113 is elastically in contact with the inner peripheral contact portion 108, at the distal side contact portion 110 in the protruding state of the hood 32, the abutting surface 105 of the elastic portion 113 is firmly appressed against the receiving surface 106. Therefore, the air-tightness is further assuredly maintained at the distal side contact portion 110. Therefore, the air is further effectively prevented from flowing to the outside of the fixed member 31 from the inside of the hood 32 and the cavity 42.

Figure 17:
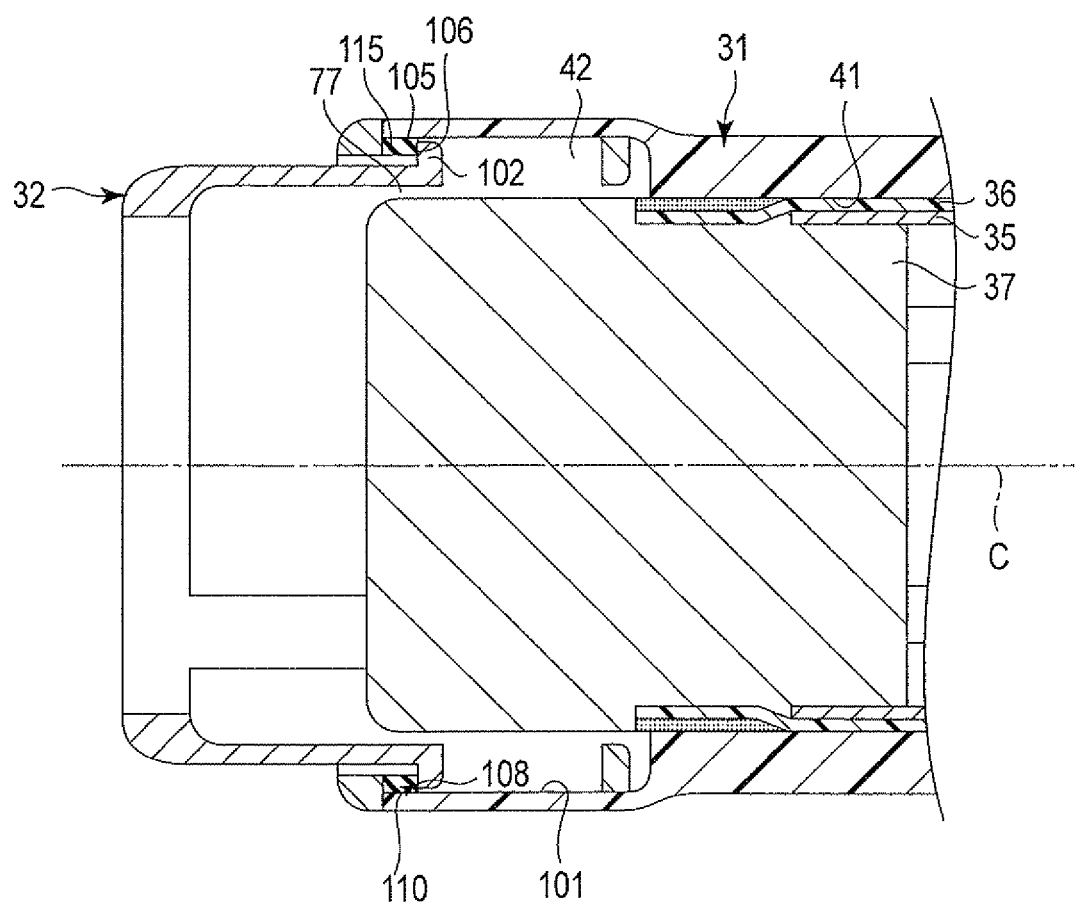
FIG. 17 is a cross-sectional view schematically showing an attachment configuration of an attachment unit with respect to an insertion section of an endoscope when a hood is in a protruding state according to a second modification of the second embodiment.

Moreover, as a second modification of the second embodiment, the fixed member 31 may include an elastic portion 115 made of an elastic material such as a rubber as shown in FIG. 17. In this modification, part of the concave portion 101 is formed of the elastic portion 115. Additionally, the receiving surface 106 at the distal end of the concave portion 101 is formed by the elastic portion 115. Further, in the protruding state of the hood 32, the abutting surface 105 of the convex portion 102 of the hood 32 abuts on the receiving surface 106 of the elastic portion 115. That is, in the protruding state of the hood 32, the elastic portion 115 of the inner peripheral contact portion 108 is elastically in contact with the convex portion 102 of the hood 32.

Since the elastic portion 115 is elastically in contact with the convex portion 102, at the distal side contact portion 110 in the protruding state of the hood 32, the receiving surface 106 of the elastic portion 115 is firmly appressed against the abutting surface 105. Therefore, at the distal side contact portion 110, the air-tightness is further assuredly maintained. Therefore, the air is further effectively prevented from flowing to the outside of the fixed member 31 from the inside of the hood 32 and the cavity 42.

Other characteristic technical matters of the present invention will now be additionally given as described below.

Note (Additional Remark 1)
An endoscopic device comprising:
an endoscope which includes an insertion section extended along a longitudinal axis;
a fixed member which is fixed to a distal end portion of the insertion section in the endoscope;
a proximal side contact portion at which an outer peripheral portion of the insertion section is in air-tight contact with the fixed member over an entire circumference in circumferential directions;
a cavity defining portion which defines a cavity to a distal direction side of the proximal side contact portion between the insertion section and the fixed member in radial directions;
a hood which is movable along the longitudinal axis with respect to the fixed member between a housed state where the hood is housed in the cavity and a protruding state where the hood is protruding toward the distal direction side;
a first path defining portion which defines a first path configured to make an inside of the hood communicate with the cavity in the protruding state of the hood;
a distal side contact portion at which the fixed member and the hood are in air-tight and liquid-tight contact with each other over the entire circumference in the circumferential directions to the distal direction side of the cavity in the protruding state of the hood; and
a second path defining portion which defines a second path between the fixed member and the hood in the radial directions in the housed state of the hood, the second path being configured to make the cavity communicate with an outside of the fixed member.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An endoscopic device comprising:
an endoscope which includes an insertion section including a distal end portion, a proximal end portion, and an outer peripheral portion and having a longitudinal axis extended from the distal end portion to the proximal end portion;
a cylindrical fixed member which includes a distal end portion, a proximal end portion, an outer peripheral portion, and an inner peripheral portion, and which is fixed to the insertion section in a state that the proximal end portion thereof contacts with the distal end portion of the insertion section;
a proximal side contact portion which is provided on the inner peripheral portion of the proximal end portion of the fixed member, and which comes into air-tight contact with the outer peripheral portion of the distal end portion of the insertion section;
a cavity defining portion which is formed by the outer peripheral portion of the insertion section and the inner peripheral portion of the distal end portion of the fixed member, and which defines a cavity between the outer peripheral portion of the insertion section and the inner peripheral portion of the distal end portion of the fixed member to a distal direction side of the proximal side contact portion;
a cylindrical hood which is movable along the longitudinal axis with respect to the fixed member between a housed state where the hood is housed in the cavity and a protruding state where the hood is protruding toward the distal direction side from the distal end portion of the fixed member;
a distal side contact portion which is provided on the inner peripheral portion of the fixed member, and with which the outer peripheral portion of the hood is in air-tight and liquid-tight contact over an entire circumference in circumferential directions in the protruding state of the hood;
a first path defining portion which is formed by the inner peripheral portion of the hood and the outer peripheral portion of the insertion section, and which defines a first path configured to make an inside of the hood communicate with the cavity in the protruding state of the hood; and
a second path defining portion which is formed by the inner peripheral portion of the fixed member and the outer peripheral portion of the hood, and which defines a second path configured to make the cavity to communicate with an outside of the fixed member in the housed state of the hood.

2. The device according to claim 1, further comprising a liquid supply path defining portion which defines a liquid supply path, through which a liquid supplied to the inside of the hood from the distal end portion of the insertion section passes, in the insertion section along the longitudinal axis.

3. The device according to claim 2,
wherein the cavity defining portion includes a liquid storage portion which is configured to allow the liquid supplied in the protruding state of the hood to flow into the cavity from the inside of the hood through the first path and configured to store the in-flowed liquid, the liquid storage portion being configured to allow the stored liquid to flow to the outside of the fixed member through the second path when the hood moves from the protruding state to the housed state.

4. The device according to claim 3,
wherein the liquid storage portion includes a concave portion which is provided over a partial range in the circumferential directions, and which is formed by concaving the inner peripheral portion of the fixed member toward an outer peripheral direction side,
the hood includes a taper portion whose dimension from the longitudinal axis to the outer peripheral portion of the hood is reduced as it goes toward the distal direction side, and
the distal side contact portion includes an inner peripheral contact portion which is provided on the inner peripheral portion of the fixed member, and with which the taper portion is in air-tight and liquid-tight contact in the protruding state of the hood.

5. The device according to claim 4,
wherein the concave portion is a plurality of concave portions provided apart from each other in the circumferential directions.

6. The device according to claim 3,
wherein the liquid storage portion includes a concave portion which is provided over the entire circumference in the circumferential directions, and which is formed by concaving the inner peripheral portion of the fixed member toward an outer peripheral direction side,
the hood includes a convex portion which is provided over the entire circumference in the circumferential directions, and which is formed by protruding the outer peripheral portion of the hood toward the outer peripheral direction side, the convex portion being configured to move in the concave portion along the longitudinal axis in accordance with movement of the hood, and
the distal side contact portion includes an inner peripheral contact portion which is provided at a distal end of the concave portion, and with which the convex portion is in air-tight and liquid-tight contact in the protruding state of the hood.

7. The device according to claim 6, further comprising:
a linear member which is provided in the insertion section along the longitudinal axis, and which is configured to move along the longitudinal axis to move the hood; and
a connecting portion which connects the linear member with the hood,
wherein the convex portion includes an abutting surface which is perpendicular to the longitudinal axis, and
the inner peripheral contact portion includes a receiving surface which is perpendicular to the longitudinal axis, and on which the abutting surface abuts in the protruding state of the hood.

8. The device according to claim 6,
wherein the convex portion includes an elastic member which is elastically in contact with the inner peripheral contact portion in the protruding state of the hood.

9. The device according to claim 6,
wherein the inner peripheral contact portion includes an elastic portion which forms part of the concave portion, and which is elastically in contact with the convex portion in the protruding state of the hood.

10. The device according to claim 1, further comprising a suction path defining portion which defines a suction path in the insertion portion along the longitudinal axis, the suction path being configured to communicate with the inside of the hood in the protruding state of the hood.

11. The device according to claim 1, further comprising:
an observation window which is provided to the distal end portion of the insertion section in the endoscope; and
an imaging element which is provided in the distal end portion of the insertion section, and which is configured to image a subject through the observation window.

12. The device according to claim 1, further comprising a movement range adjustment portion which is configured to adjust a movement range of the hood along the longitudinal axis.

13. The device according to claim 12,
wherein the movement range adjustment portion includes:
a concave portion formed by concaving the inner peripheral portion of the fixed member toward an outer peripheral direction side; and
a convex portion which is formed by protruding the outer peripheral portion of the hood toward the outer peripheral direction side, and which is configured to move in the concave portion along the longitudinal axis in accordance with movement of the hood, the convex portion being configured to abut on the concave portion to regulate the movement.

14. The device according to claim 12, further comprising:
a linear member which is provided in the insertion section along the longitudinal axis, and which is configure dot move along the longitudinal axis to move the hood;
a connecting portion which connects one end of the linear member with the hood; and a drive portion to which the other end of the linear member is connected, and which is driven when a movement operation of moving the hood is input, the drive portion being configured to move integrally with the linear member when it is driven, wherein the endoscope includes an operating section provided to a proximal direction side of the insertion section, and the movement range adjustment portion includes a regulating portion which is provided to the operating section of the endoscope or is fixed to the operating section, and which is configured to regulate a movement range of the drive portion.

\* \* \* \* \*